US00PP15630P2

(12) United States Plant Patent
Hanes

(10) Patent No.: US PP15,630 P2
(45) Date of Patent: Mar. 8, 2005

(54) ***GERANIUM* PLANT NAMED 'CLIPS WHITSPLA'**

(50) Latin Name: *Pelargonium×hortorum*
Varietal Denomination: Clips Whitspla

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/818,501

(22) Filed: Apr. 5, 2004

(51) Int. Cl.[7] ..... A01H 5/00
(52) U.S. Cl. ..... Plt./324
(58) Field of Search ..... Plt./324

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Geranium* plant named 'Clips Whitspla', characterized by its upright, outwardly spreading and rounded growth habit; freely basal branching habit; dark green-colored leaves; freely flowering habit with many flower umbels per plant; and flower umbels with numerous white and red purple bi-colored single flowers.

1 Drawing Sheet

Botanical classification/cultivar designation: *Pelargonium×hortorum* cultivar Clips Whitspla.

BACKGROUND OF THE INVENTION

The present invention relates to a new and distinct cultivar of *Geranium* plant, botanically known as *Pelargonium× hortorum,* commercially known as a Zonal *Geranium*, and hereinafter referred to by the name 'Clips Whitspla'.

The new *Geranium* is a product of a planned breeding program conducted by the Inventor in Gilroy, Calif. The objective of the breeding program is to develop new Zonal *Geranium* cultivars with good basal branching, freely flowering habit and attractive flower and foliage coloration.

The new *Geranium* originated from a cross-pollination made by the Inventor in April, 2000 of a proprietary *Pelargonium×hortorum* selection identified as code number 8553-1, not patented, as the female, or seed, parent with the *Pelargonium×hortorum* cultivar BFP-1700, disclosed in U.S. Plant Pat. No. 11,397, as the male, or pollen, parent. The cultivar Clips Whitspla was discovered and selected by the Inventor as a flowering plant within the progeny from this cross-pollination in a controlled environment in Gilroy, Calif. in September, 2000.

Asexual reproduction of the new cultivar by terminal cuttings at Gilroy, Calif., since September, 2000 has shown that the unique features of this new *Geranium* are stable and reproduced true to type in successive generations of asexual reproduction.

SUMMARY OF THE INVENTION

The following traits have been repeatedly observed and are determined to be the unique characteristics of 'Clips Whitspla'. These characteristics in combination distinguish 'Clips Whitspla' as a new and distinct *Geranium* cultivar:

1. Upright, outwardly spreading and rounded growth habit.
2. Freely basal branching habit.
3. Dark green-colored leaves.
4. Freely flowering habit with many large flower umbels per plant.

5. Flower umbels with numerous white and red purple bi-colored single flowers.

In side-by-side comparisons conducted in Gilroy, Calif., plants of the new *Geranium* differed from plants of the female parent selection in the following characteristics:

1. Plants of the new *Geranium* were more vigorous than plants of the female parent selection.
2. Plants of the new *Geranium* had single flowers whereas plants of the female parent selection had semi-double flowers.

In side-by-side comparisons conducted in Gilroy, Calif., plants of the new *Geranium* differed from plants of the male parent, the cultivar BFP-1700, in the following characteristics:

1. Plants of the new *Geranium* were more vigorous than plants of the cultivar BFP-1700.
2. Plants of the new *Geranium* had lighter green-colored leaves than plants of the cultivar BFP-1700.

The new *Geranium* can be compared to the cultivar, Americana White Splash, disclosed in U.S. Plant Pat. No. 9,317. However, in side-by-side comparisons conducted in Gilroy, Calif., plants of the new *Geranium* differed from plants of the cultivar Americana White Splash in the following characteristics:

1. Plants of the new *Geranium* had darker green-colored leaves than plants of the cultivar Americana White Splash.
2. Flowers of plants of the new *Geranium* were more open in form than flowers of plants of the cultivar Americana White Splash.
3. Flowers of plants of the new *Geranium* had smaller red purple spots than flowers of plants of the cultivar Americana White Splash.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical flowering plant of 'Clips Whitspla'.

The photograph at the bottom of the sheet is a close-up view of typical flower umbels and leaves of 'Clips Whitspla'.

Flower and foliage colors in the photographs may differ slightly from the color values cited in the detailed botanical description which accurately describe the colors of the new *Geranium*.

DETAILED BOTANICAL DESCRIPTION

Plants of the cultivar Clips Whitspla have not been observed under all possible environmental conditions. The phenotype may vary somewhat with variations in environment such as temperature and light intensity, without, however, any variance in genotype. The aforementioned photographs and following observations and measurements describe plants grown in Gilroy, Calif., under commercial practice in a fiberglass-covered greenhouse during the late spring with day temperatures about 27 to 29° C., night temperatures about 16 to 18° C. and light levels about 2,000 foot-candles. Plants used for the photographs and description were about six months from planting rooted cuttings. In the following description, color references are made to The Royal Horticultural Society Colour Chart, 1995 Edition, except where general terms of ordinary dictionary significance are used.

Botanical classification: *Pelargonium×hortorum* cultivar Clips Whitspla.

Parentage:

*Female parent.*—Proprietary *Pelargonium×hortorum* selection identified as code number 8553-3, not patented.

*Male parent.*—*Pelargonium×hortorum* cultivar BFP-1700, disclosed in U.S. Plant Pat. No. 11,397.

Propagation:

*Type cutting.*—Terminal cuttings.

*Time to initiate roots.*—About 12 to 14 days at 24° C.

*Time to develop roots.*—About four weeks at 18 to 24° C.

*Root description.*—Fibrous, fine; white in color.

*Rooting habit.*—Freely branching.

Plant description:

*General appearance.*—Upright, outwardly spreading and rounded growth habit.

*Growth and branching habit.*—Vigorous and very freely basal branching with about 12 lateral branches. Pinching, that is, removal of terminal apices, is typically not required.

*Plant height to top of foliage.*—About 27 cm.

*Plant height to top of flower umbels.*—About 32 cm.

*Plant width.*—About 46 cm.

*Lateral branches.*—Length: About 20 cm. Diameter: About 1 cm. Internode length: About 2 mm. Texture: Pubescent. Color: 146D.

*Foliage description.*—Arrangement: Alternate, simple. Length: About 6.8 cm. Width: About 11.5 cm. Shape: Reinform with slight rounded lobes. Apex: Rounded. Base: Truncate to cordate. Margin: Crenate. Venation: Palmate. Texture, upper and lower surfaces: Velvety; pubescent; somewhat leathery. Color: Developing foliage, upper surface: 147A. Developing foliage, lower surface: 147B. Fully developed foliage, upper surface: Darker than 147A. Fully developed foliage, lower surface: 146A. Venation, upper surface: 146A. Venation, lower surface: 146B. Petiole: Length: About 14 cm. Diameter: About 3 mm. Texture, upper and lower surfaces: Pubescent. Color, upper and lower surfaces: 146B.

Flower description:

*Flower arrangement and type.*—Single rounded flowers arranged in hemispherical umbels arising from apical leaf axils. Umbels displayed above the foliage. At full flowering, usually about 16 open and developing umbels per plant. Flowers not persistent; umbels persistent. Flowers not fragrant.

*Flowering season.*—Year-round under greenhouse conditions. In the garden, flowering is continuous from spring until fall. Plants start flowering about eight weeks after planting.

*Flower longevity.*—Flowers last about one week on the plant.

*Umbels.*—Height: About 8 cm. Diameter: About 13 cm. Number of flowers and flower buds per umbel: Very freely flowering, about 44. Flower diameter: About 4.75 cm. Flower depth (height): About 3 cm.

*Flower buds.*—Length: About 2.3 cm. Diameter: About 1 cm. Shape: Ovoid. Color: 155D with venation, 57A.

*Petals.*—Quantity/arrangement: About five petals in a single whorl. Length: About 2.2 cm. Width: About 2 cm. Shape: Obovate. Apex: Rounded. Base: Acute. Margin: Entire; slightly ruffled. Texture, upper and lower surfaces: Smooth; satiny. Aspect: Upper two petals, reflexed; lower three petals, slightly cupped. Color: When opening, upper surface: More white than 155D; spots/splotches, 57A. When opening, lower surface: More white than 155D. Fully opened, upper surface: More white than 155D; spots/splotches, 57A to 57C; venation, 155D and 60B, that is, similar to petal color. Fully opened, lower surface: More white than 155D; venation, 57A.

*Sepals.*—Quantity/arrangement: Five per flower in a single whorl; not imbricate on open flowers. Length: About 1.2 cm. Width: About 3 mm. Shape: Narrowly elliptic. Apex: Acuminate. Margin: Entire. Texture, upper and lower surfaces: Pubescent. Color, upper and lower surfaces: 144A.

*Peduncle* (*umbel stem*).—Length: About 14.5 cm. Diameter: About 4 mm. Angle: About 30° from vertical. Strength: Strong. Texture: Pubescent. Color: 146B.

*Pedicel* (*individual flower stem*).—Length: About 5 cm. Diameter: About 1.5 mm. Angle: Erect to about 90° from vertical. Strength: Strong. Texture: Pubescent. Color: 146B.

*Reproductive organs.*—Androecium: Anther quantity: About five per flower. Anther size: About 1 by 2 mm. Anther shape: Oval. Anther color: 48B. Pollen amount: Scarce. Pollen color: 31A. Gynoecium: Pistol quantity: One per flower. Pistil length: About 1.1 cm. Stigma shape: Five-parted, star-shaped. Stigma color: 39C. Style length: About 4 mm. Style color: 39C. Ovary color: 138B.

*Seed/fruit.*—Seed and fruit development has not been observed.

Disease/pest resistance: Resistance to pathogens and pests common to *Pelargonium* has not been observed.

It is claimed:

1. A new and distinct cultivar of *Geranium* plant named 'Clips Whitspla', as herein illustrated and described.

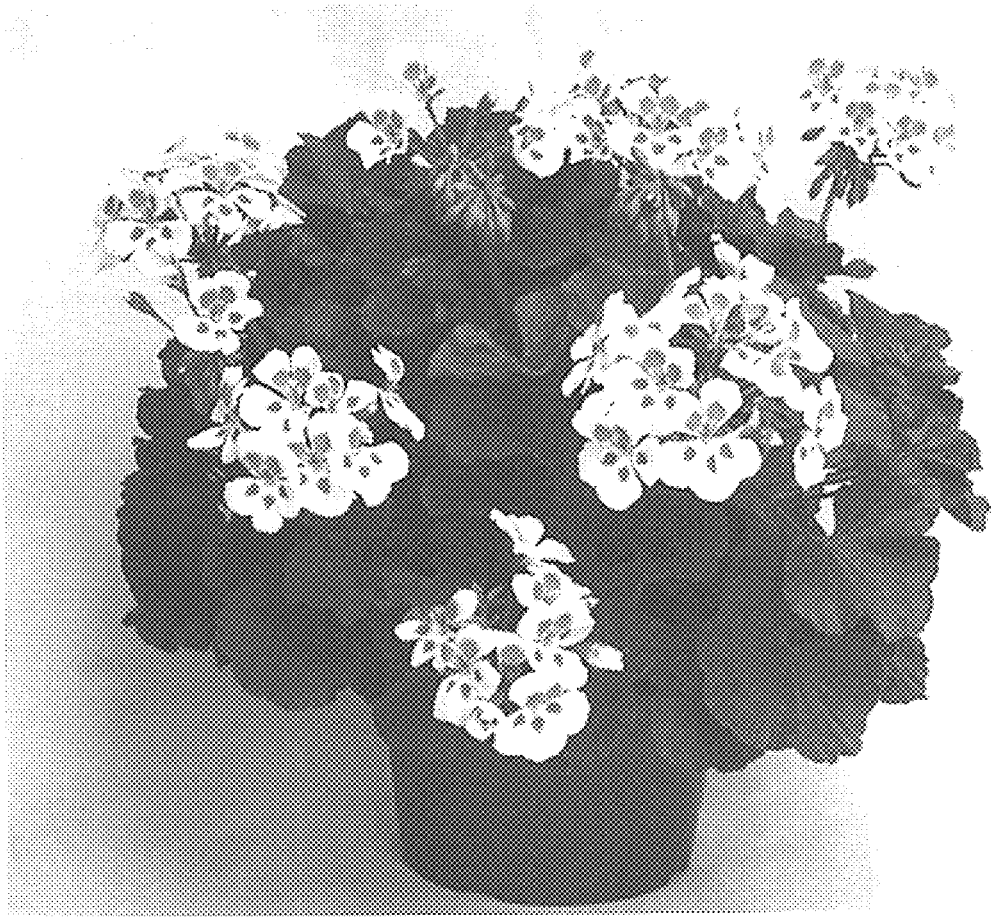
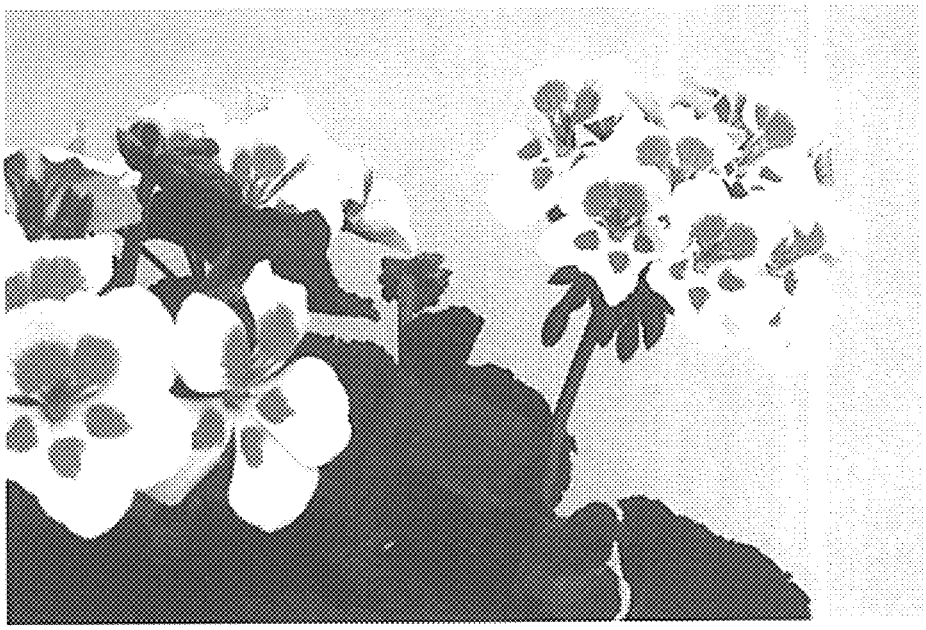

* * * * *